(12) United States Patent
Weber et al.

(10) Patent No.: US 8,562,566 B2
(45) Date of Patent: Oct. 22, 2013

(54) STENT DELIVERY AND GUIDEWIRE GUIDANCE SYSTEM

(75) Inventors: Jan Weber, Maple Grove, MN (US); Raed Rizq, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2098 days.

(21) Appl. No.: 11/068,330

(22) Filed: Feb. 28, 2005

(65) Prior Publication Data

US 2008/0009770 A1    Jan. 10, 2008

(51) Int. Cl.
*A61M 5/178*    (2006.01)

(52) U.S. Cl.
USPC ................................. 604/164.01

(58) Field of Classification Search
USPC ........... 604/164.01, 164.03, 523, 524, 103.09
See application file for complete search history.

(56) References Cited

U.S. PATENT DOCUMENTS

| | | | |
|---|---|---|---|
| 4,748,982 A | 6/1988 | Horzewski et al. | 128/344 |
| 4,946,443 A | 8/1990 | Hauser et al. | 604/165 |
| 4,988,356 A | 1/1991 | Crittenden et al. | 606/192 |
| 5,171,222 A | 12/1992 | Euteneuer et al. | 604/102 |
| 5,176,660 A | 1/1993 | Truckai | |
| 5,221,255 A * | 6/1993 | Mahurkar et al. | 604/43 |
| 5,316,023 A | 5/1994 | Palmaz et al. | 128/898 |
| 5,334,187 A | 8/1994 | Fischell et al. | 604/194 |
| 5,554,118 A | 9/1996 | Jang | 604/96 |
| 5,569,296 A | 10/1996 | Marin et al. | |
| 5,609,627 A | 3/1997 | Goicoechea et al. | 623/1 |
| 5,749,825 A | 5/1998 | Fischell et al. | 600/3 |
| 5,921,971 A | 7/1999 | Agro et al. | 604/280 |
| 6,007,517 A | 12/1999 | Anderson | 604/96 |
| 6,007,522 A | 12/1999 | Agro et al. | 604/264 |
| RE36,857 E | 9/2000 | Euteneuer et al. | 604/102 |
| 6,143,002 A | 11/2000 | Vietmeier | 606/108 |
| 6,312,404 B1 | 11/2001 | Agro et al. | 604/95.02 |
| 6,346,093 B1 | 2/2002 | Allman et al. | 604/167.06 |
| 6,520,983 B1 | 2/2003 | Colgan et al. | 623/1.11 |
| 6,605,062 B1 | 8/2003 | Hurley et al. | 604/164.13 |
| 6,746,442 B2 | 6/2004 | Agro et al. | 604/523 |
| 6,764,484 B2 | 7/2004 | Richardson et al. | 604/523 |
| 6,800,065 B2 | 10/2004 | Duane et al. | 604/96.01 |
| 6,849,077 B2 | 2/2005 | Ricci | 606/108 |
| 7,018,372 B2 * | 3/2006 | Casey et al. | 604/524 |
| 7,131,986 B2 * | 11/2006 | Sirhan et al. | 606/194 |
| 7,229,431 B2 * | 6/2007 | Houser et al. | 604/103.04 |
| 2003/0149444 A1 | 8/2003 | Khaw | |
| 2004/0220653 A1 | 11/2004 | Borg et al. | |

FOREIGN PATENT DOCUMENTS

| | | |
|---|---|---|
| EP | 0 876 804 A1 | 11/1998 |
| EP | 1 306 062 A1 | 5/2003 |
| WO | WO 2005/039681 A1 | 5/2005 |

* cited by examiner

*Primary Examiner* — Kevin C Sirmons
*Assistant Examiner* — Bradley Osinski
(74) *Attorney, Agent, or Firm* — Seager, Tufte & Wickhem LLC

(57) ABSTRACT

A system for controlling multiple guidewires comprises a guiderail, which has a housing that defines a first guidewire lumen and a second guidewire lumen. The guidewire lumens extend through the entire length of the guiderail. The guiderail housing further defines a first longitudinal opening that extends from the first guidewire lumen to the exterior of the guiderail, and a second longitudinal opening that extends from the second guidewire lumen to the exterior of the guiderail.

9 Claims, 11 Drawing Sheets

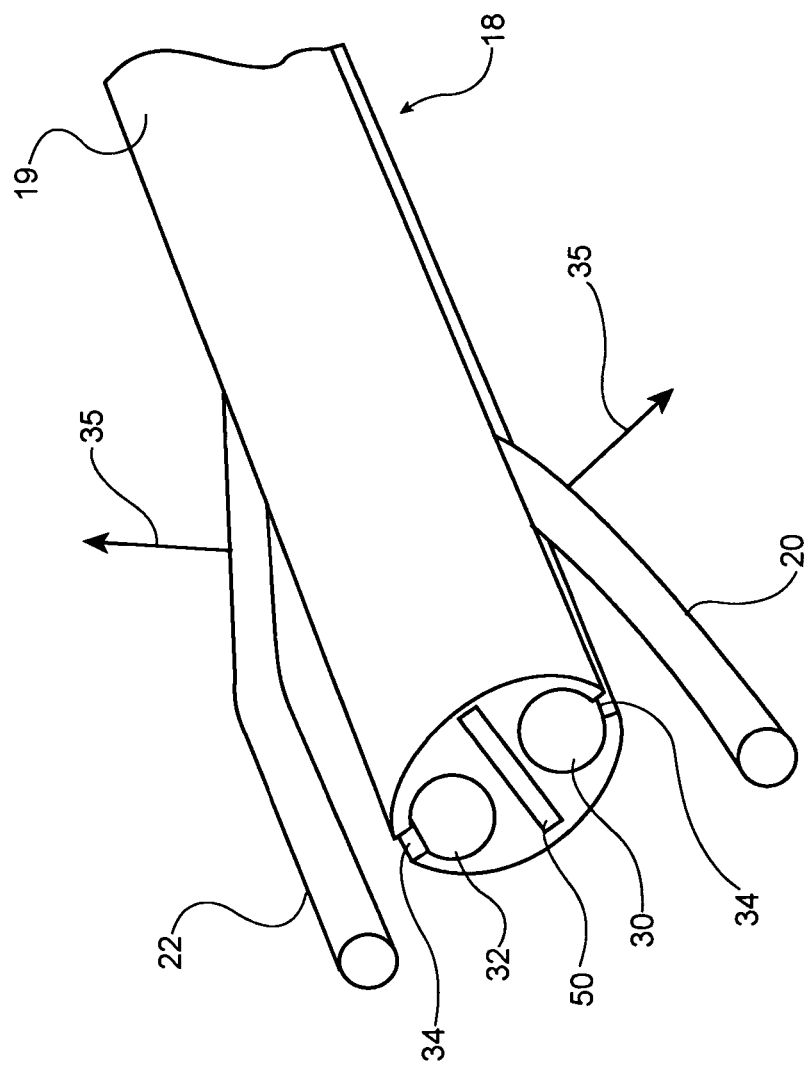

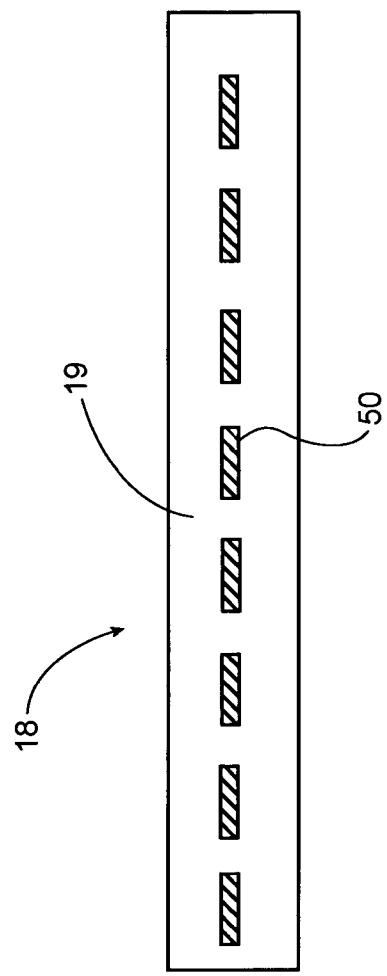

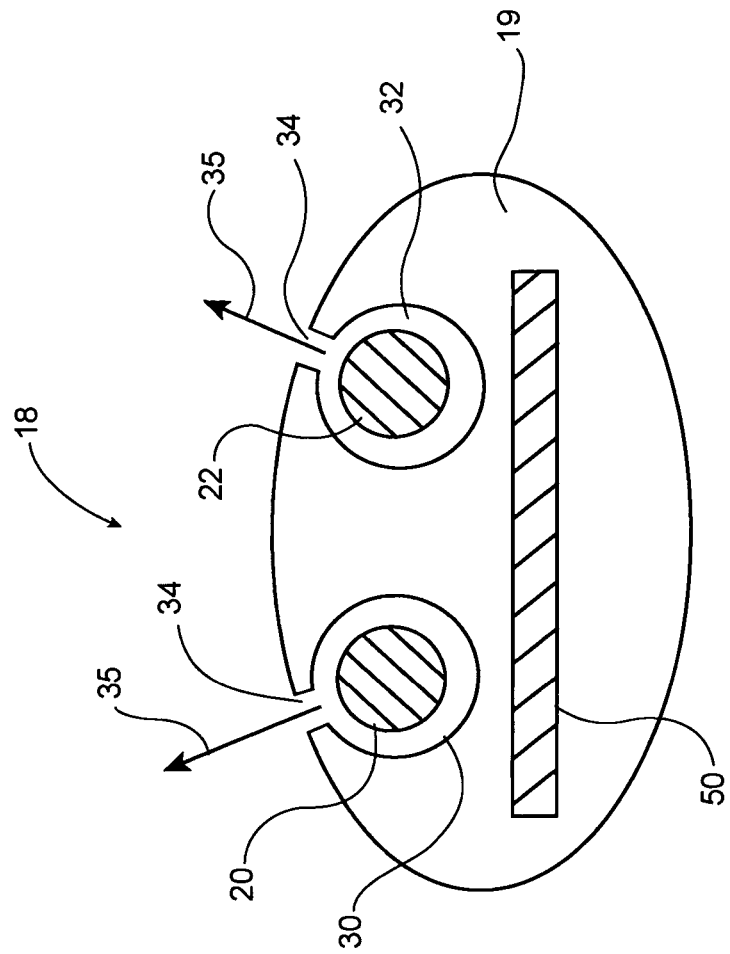

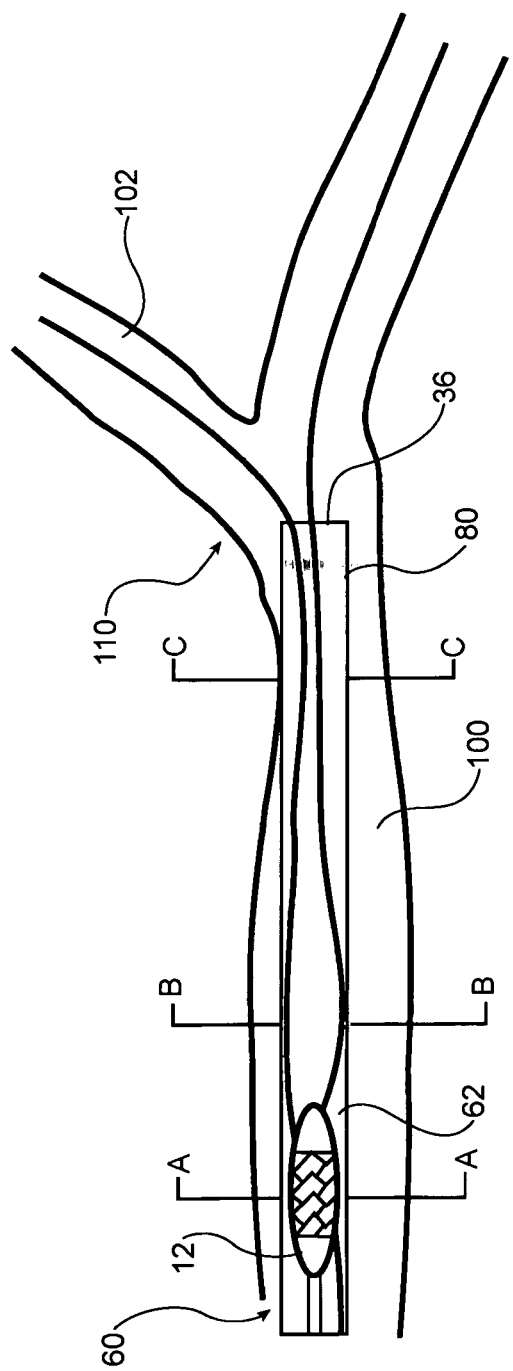

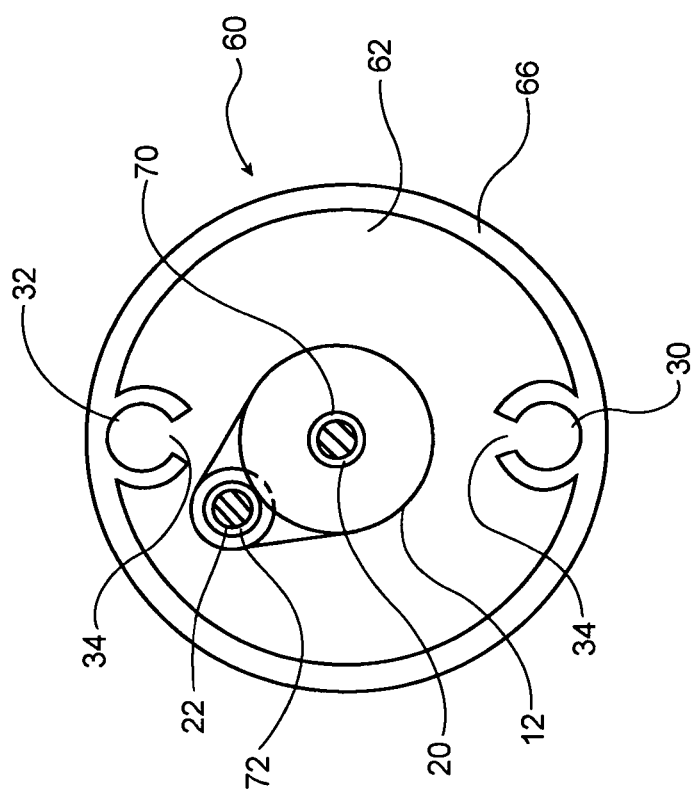

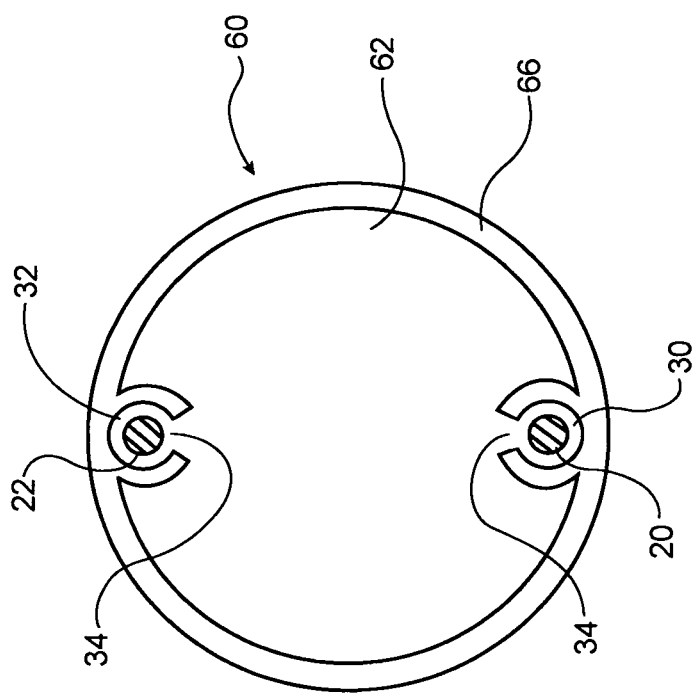

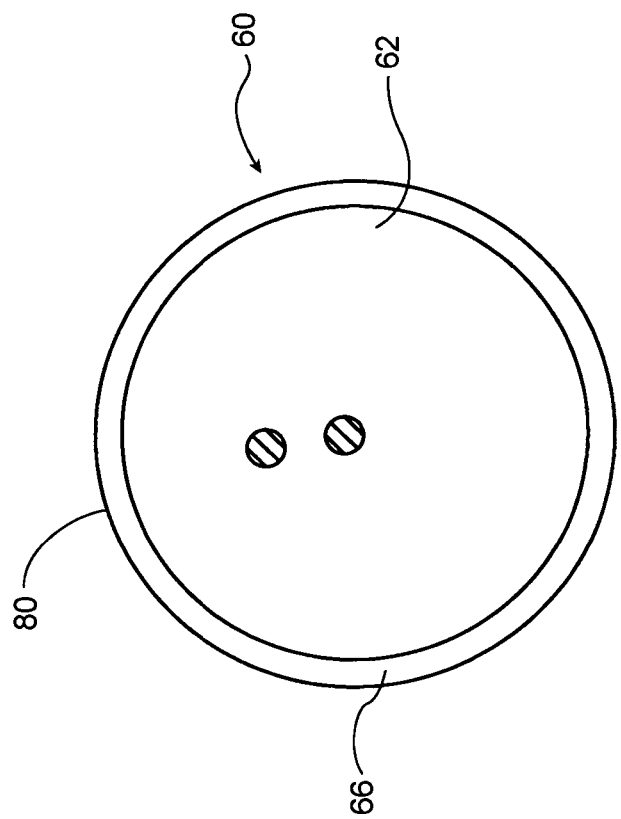

STENT DELIVERY AND GUIDEWIRE GUIDANCE SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

At least one embodiment of the present invention is directed to the field of stents and stent delivery systems, and more particularly to systems for the treatment of a bifurcation of a passage and/or ostium of vessel.

2. Description of the Related Art

Stent systems are widely used in the treatment of stenoses. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

It is recognized, however, that a stent can be deployed in manners other than inflating and deflating a balloon. For example, self-expanding stents have been developed in which a cover is removed from over a stent, thereby allowing the stent to deploy or spring into place. It is also contemplated that other deployment mechanisms or means may be used or developed to advantageously deliver and deploy a stent in position.

Nevertheless, a need still exists for properly delivering and locating a stent at a bifurcation. Although efforts have been made to use a stent at bifurcations, these sites have previously been inadequately treated by a stent. For example, U.S. Pat. No. 5,749,825 is representative of a catheter system that treats stenoses at an arterial bifurcation. The disclosure of U.S. Pat. No. 5,749,825 is hereby incorporated by reference.

Delivery of a stent to a vessel bifurcation will often employ a pair of guidewires (a primary, or main-branch, guidewire positioned in the main branch of the vessel and a secondary, or side-branch, guidewire advanced into the side branch vessel of the bifurcation) upon which the delivery catheter is advanced. The divergent paths of the guidewires at the vessel bifurcation aid in orienting the delivery catheter such that the side branch opening of the stent to be delivered is properly aligned with the side branch vessel.

One of the problems encountered with placing a stent in a bifurcation is the potential for the guidewires to become twisted and/or knotted. As a catheter is advanced along the guidewires the catheter may push the crossings of the guidewires all the way to vessel bifurcation resulting in an entanglement which prevents the catheter from being advanced beyond the bifurcation and preventing proper alignment of the stent to be delivered.

Thus, a need exists for a system which reduces wire crossing during the advancement of a stent delivery catheter.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is embodied in a variety of forms. In at least one embodiment the invention is directed to a new and improved guidewire guidance system for use with catheters and stent delivery systems for advancement and orientation at vessel bifurcations.

In at least one embodiment a guidance system comprises a guiderail that defines a primary guidewire lumen and a secondary guidewire lumen. The lumens are not completely closed and are configured to allow the wires to be pulled out or "unzipped" through the respective sides of the guiderail housing.

In at least one embodiment the lumens are substantially C-shaped.

In at least one embodiment the lumens are of different diameters to accommodate the passage of different sized guidewires therein.

In some embodiments the guiderail housing is at least partially constructed of a flexible polymer material. Some examples of suitable materials include but are not limited to: PVC; polyether block amides such as PEBAX® 25D, 30D, 40D, etc.; polyurethane; pellethane; polyethylene; etc.

In at least one embodiment the guiderail comprises a stiffer segment, constructed of a material having a greater stiffness than that of the flexible polymer material. In some embodiments the stiffer segment is at least partially constructed of a material having a greater hardness than that of the flexible polymer material. In at least one embodiment the "stiffer" segment is at least partially constructed of a shape-memory polymer or metal such as nitinol. The stiffer segment is configured to provide bending flexibility in at least one direction but at the same time torsional rigidity to the guiderail assembly. In some embodiments the stiffer segment is at least partially constructed from a filled polymer such as nylon 11 filed with carbon nanotubes, for improved performance in magnetic resonance imaging applications. Examples of some other materials suitable for use in forming the stiffer segment include but are not limited to: steel; polymers such as HDPE, nylon 12, polycarbonate, etc.

In at least one embodiment the stiffer segment is positioned substantially between the guidewire lumens.

In at least one embodiment the lumens are positioned on the same side of the stiffer segment.

In at least one embodiment the stiffer segment provides increased torsional rigidity to the rail.

A method of using a guiderail comprises first advancing the main guidewire in to the vessel and then sliding the guiderail over the main guidewire up to the point of the vessel bifurcation. The secondary guidewire is then advanced through the secondary guidewire lumen of the guiderail where it exits the distal end of the guiderail and is advanced into the sidebranch vessel. A stent delivery catheter is then advanced along the guidewires simultaneously. As the catheter slides over the wires, each wire is forced out of the respective side openings of the lumens. By the time the delivery catheter reaches the bifurcation the wires will be completely removed from the lumens of the guiderail and the guiderail may then be removed. The presence of the guiderail during catheter advancement prevents the guidewires from twisting around each other and eliminates the occurrence of knots, loops or crossings of the wires.

In some embodiments, the guiderail is embodied as a hollow tube such as a guide catheter. The inside surface of the guide catheter comprises one or more rails, which define the primary and/or secondary guidewire lumens. The wires are capable of unzipping from the rail lumens in the manner previously described.

These and other embodiments which characterize the invention are pointed out with particularity in the claims annexed hereto and forming a part hereof. However, for additional understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIG. 2 is a cross-sectional perspective view of the guiderail depicted in FIG. 1 with the guidewires shown exiting therefrom.

FIG. 4 is a longitudinal cross-sectional view of an embodiment of the guiderail.

FIG. 5 is a cross-sectional view of an embodiment of the guiderail.

FIG. 6 is a longitudinal, partial cross-section view of an embodiment of the invention shown in use at a vessel bifurcation.

FIG. 7A is a cross-sectional view of the portion of the embodiment shown in FIG. 6 corresponding to line A.

FIG. 7B is a cross-sectional view of the portion of the embodiment shown in FIG. 6 corresponding to line B.

FIG. 7C is a cross-sectional view of the portion of the embodiment shown in FIG. 6 corresponding to line C.

DETAILED DESCRIPTION OF THE INVENTION

Figure 1:
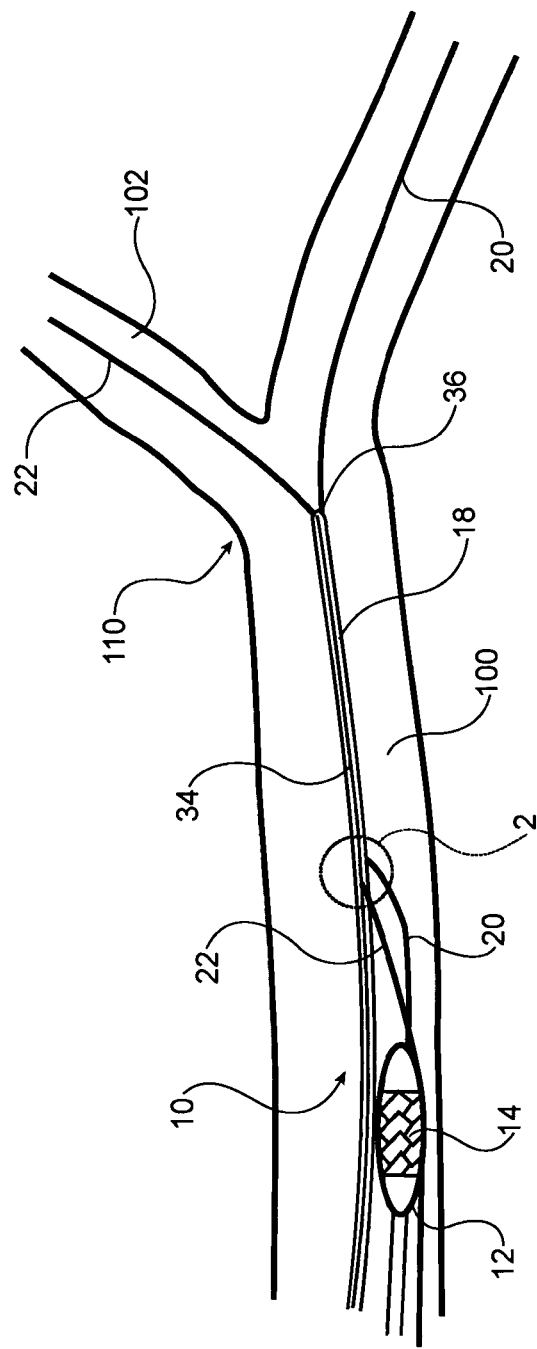
FIG. 1 is a longitudinal, partial cross-section view of an embodiment of the invention shown in use at a vessel bifurcation.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In at least one embodiment of the invention, an example which is illustrated in FIG. 1 a bifurcation 110 of a primary vessel 100 and a secondary vessel 102 is shown. Within the primary vessel 100, a stent delivery system 10 comprising a stent delivery catheter 12 and stent 14, is shown being advanced to the region of the bifurcation 110. To properly position the stent 14 for deployment at the vessel bifurcation 110 the catheter 12 is advanced, along a primary guidewire 20 and a secondary guidewire 22. The guidewires 20 and 22 diverge at the bifurcation 110, with the distal portion of the primary guidewire 20 extending distally beyond the vessel bifurcation 110 and the distal portion of the secondary guidewire 22 branching off from the primary vessel 100 and extending into the branch vessel 102 at the bifurcation 110.

In the embodiment shown in FIG. 1, the system 10 further comprises a guiderail 18 which extends proximally from the bifurcation 110 of the vessels to the exterior of the patient's body (not shown).

Figure 3A:
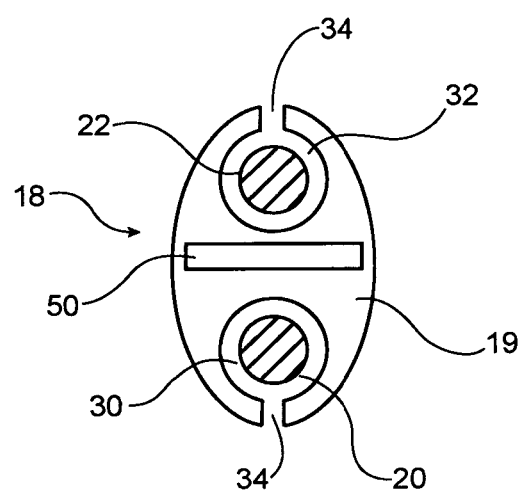
FIGS. 3A-3C are a series of cross-sectional views depicting the manner in which guidewires may exit the guiderail of FIG. 2.
Figure 3B:
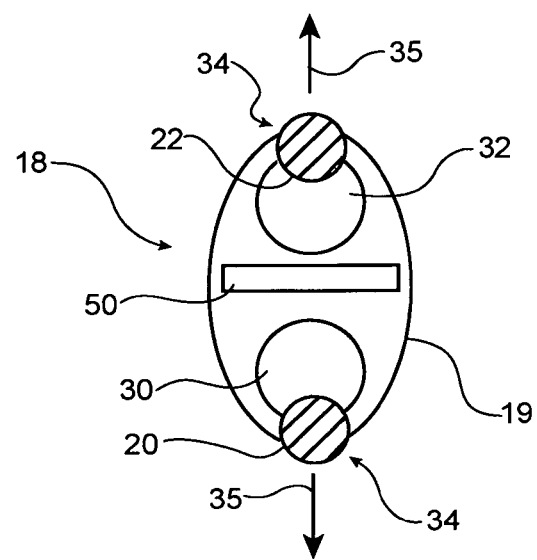
Figure 3C:
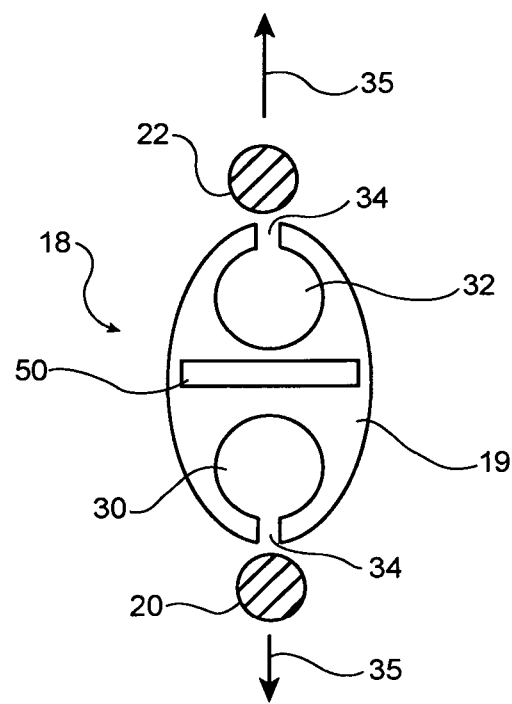

As is shown in FIG. 2, in some embodiments the guiderail 18 is comprised of a polymeric housing 19 which defines a primary guidewire lumen 30 for passage of the primary guidewire 20 therethrough, and a secondary guidewire lumen 32 for passage of the secondary guidewire 22 therethrough. The housing 19 is configured such that each lumen 30 and 32 is provided with a longitudinal slit or gap 34 that provides an opening from a given lumen to the guiderail exterior. Through the gap 34 in each lumen 30 and 32 the guidewires 20 and 22 may be pulled out in a somewhat lateral direction, as indicated by arrows 35, from their respective lumens 30 and 32, such as in the manner shown in FIG. 1-3.

In at least one embodiment the longitudinal slit 34 is an opening in the guiderail housing 19 which extends into the respective lumen 30 and 32. The width of the slit will nominally be less than that of a guidewire, but the polymeric nature of the housing 19 allows the slit 34 to be distorted or widened to allow the guidewire to be pulled therethrough without detriment.

In at least one embodiment the polymeric nature of the housing 19 provides the longitudinal slit 34 of the lumens 30 and 32 to be effectively "closed" but when acted upon by sufficient force the guidewires 20 and 22 will force the slit 34 open to allow the guidewires 20 and 22 to be "unzipped" from their respective lumens 30 and 32 in the manner shown in FIGS. 1-2 and 3A-3C. The force which pulls the guidewires 20 and 22 out of the lumens 30 and 32 is provided by the passage of the catheter 12 along the guidewires 20 and 22 relative to the guiderail 18, such as is illustrated in FIG. 1

As is illustrated in FIG. 1, in practice the guiderail 18 is held in position within the primary vessel 100 while the guidewires 20 and 22 exit the lumens at the distal end 36 of the guiderail 18 proximally adjacent to the bifurcation 110. As the catheter 12 is advanced through the vessel 100 along the guidewires 20 and 22, the guidewires 20 and 22 will be drawn out from the lumens 30 and 32, through the slits 34, such as in the manner shown in FIGS. 2-3.

Positioning of the guiderail 18 within the vessel 100 may be accomplished by advancing the guiderail along the primary guidewire 20, after the guidewire 20 has been inserted into the vessel 100 in the manner shown in FIG. 1. Once the guiderail 18 is properly positioned on the primary guidewire 20, with the distal end 36 of the guiderail 18 positioned proximally adjacent to the bifurcation 110, the secondary guidewire 22 may be advanced through the secondary lumen 32. The secondary guidewire 22 exits the lumen 32 at the distal end 36 of the guiderail and is ten advanced into the branch vessel 102. Once the guidewires 20 and 22 as well as the guiderail 18 are in position, the catheter 12 may be advanced to the bifurcation 110 in the manner described above.

In some embodiments it may be desirable to provide the guiderail 18 greater longitudinal rigidity or stiffness than the polymeric material of the housing 19 will otherwise provide. Such increased stiffness may improve the push characteristics of the guiderail 18 for improved advancement through body lumens. In at least one embodiment, an example of which is shown in FIGS. 2-3, such an increase in stiffness may be provided by including within the guiderail 18 a segment 50 of relatively hard or stiffer material within the softer or more flexible material of the housing 19.

While an increase in longitudinal stiffness may be desired in some embodiments, it is necessary to maintain axial flexibility so that the guiderail is capable of flexing and bending as it is advanced through the potentially tortuous confines of the vessel 100. In some embodiments the stiffer segment 50 is a continuous strip extending along the length of the guiderail 18. However, depending on the flexibility and stiffness characteristics of the housing 19 and the segment 50, a non-continuous or segmented structure for the segment 50 may be desired, such as is shown in FIG. 4. The segmented nature of the segment 50 provides the desired longitudinal stiffness but also allows the guiderail sufficient flexibility to bend and flex laterally.

In some embodiments the segment 50 also provides the guiderail 18 with increased torsional rigidity. In the embodiment depicted in FIGS. 2-3, the rectangular cross-sectional shape of the segment 50 provides the guiderail with an inherent mechanism for rotationally biasing or torquing the guiderail 18 from outside the body during advancement.

In some embodiments each lumen 30 and 32 are positioned on opposite sides of the stiffer segment 50. In at least one embodiment however, an example of which is shown in FIG. 5, the lumens 30 and 32 are on the same side of the stiffer segment 50. The relative positions of the lumens 30 and 32 in the guiderail housing 19 may be varied depending on the orientation of the vessels 100 and 102 at the vessel bifurcation 110, and on the cross-sectional shape of the guiderail 18 itself.

In at least one embodiment of the invention, an example of which is shown in FIGS. 6 and 7A-7C, the guiderail may be configured as a guide catheter 60, which defines a central lumen 62, through which the catheter 12 is advanced. In this configuration, the guide catheter 60 comprises a housing 66, which is configured to define the lumens 30 and 32. The longitudinal slit 34 of each lumen opens into the central lumen 62.

In the configuration shown in FIG. 6, initially the primary guidewire 20 is inserted into the primary vessel 100 and extends distally beyond the bifurcation. The guide catheter 60 is then advanced along the primary guidewire 20 via the primary guidewire lumen 30. The secondary guidewire 22 is then passed through the secondary guidewire lumen 32, where it exits the lumen 32 at the distal end 36 of the guide catheter and is advanced into the branch vessel 102 at the bifurcation 110. Following placement of the guidewires 20 and 22 and the guide catheter 60, the catheter 12 can be advanced through the catheter lumen 62 to the bifurcation 110 along the guidewires 20 and 22.

As is shown in FIG. 7B, the guidewires 20 and 22 will remain in their respective lumens 30 and 32, until the advancement of the catheter 12 pulls the guidewires through the slit 34 of the lumens 30 and 32 and into the central lumen 62. As shown in FIG. 7A the guidewires 20 and 22 will be drawn into the (guidewire) tracking lumens 70 and 72 of the catheter itself as the catheter 12 is advanced through the catheter lumen 62 of the guide catheter 60.

In at least one embodiment the distal end 36 of the guide catheter 60 comprises a tip 80 which is at least partially constructed of a softer material than that of the guide catheter housing 66. The relatively soft nature of the tip 80 provides improved flexibility to the distal end of the guide catheter and provides additional protection to the vessel(s) where the guidewires diverge from the guide catheter. As is shown in FIG. 7C, in at least one embodiment, the tip 80 does not define distinct guidewire lumens.

In addition to the above, it should be recognized that the guide rail assembly described herein may be modified and reconfigured in a variety of ways. For example, in at least one embodiment the guiderail may be configured to accommodate more than two guidewires. In at least one embodiment the guiderail may be configured to provide an additional lumen for the passage of a fiber optic viewing system; and or mechanisms for the cutting or manipulation of tissue. In at least one embodiment the guiderail assembly may be configured with a plurality of lumens such that it could be utilized to feed multiple systems.

The invention has been described with reference to the preferred embodiments. Obviously, modifications and alterations will occur to others upon a reading and understanding of this specification. For example, the illustrated embodiments use a balloon to expand the stent although, as briefly noted above, a self expanding or self deploying stent can be used without departing from the features of the present invention. Likewise, using a fixed wire on the distal end of the apparatus is also recognized as being consistent with the features of the present invention. Moreover, the preferred embodiments describe various components such as a balloon, catheter shaft, barrel, etc. The components of the various embodiments may be constructed from any of a wide variety of materials including polymers, metals etc.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A system for advancing a medical device over multiple guidewires, the system comprising:

a first guidewire;

a second guidewire;

a guiderail having a length and including a guiderail housing, the guiderail housing defining a first guidewire lumen and a second guidewire lumen, both the first guidewire lumen and the second guidewire lumen extending the entire length of the guiderail, wherein the guiderail housing defines a first longitudinal opening extending from the first guidewire lumen to an exterior of the guiderail along the entire length of the first guidewire lumen and a second longitudinal opening extending from the second guidewire lumen to the exterior of the guiderail along the entire length of the second guidewire lumen, wherein the guiderail is configured to be advanced over at least one of the first guidewire and the second guidewire in a vessel; and a catheter having a first guidewire lumen configured to receive the first guidewire and a second guidewire lumen configured to receive the second guidewire, wherein the catheter is configured to be advanced over the first guidewire and the second guidewire to a target region in the vessel, wherein the advancement of the catheter over the first guidewire and the second guidewire pulls the first guidewire completely out of the first guidewire lumen through the first longitudinal opening and pulls the second guidewire completely out of the second guidewire lumen through the second longitudinal opening.

2. The system of claim 1 wherein the second guidewire is advanced through the second guidewire lumen of the guiderail after the guiderail is advanced over the first guidewire.

3. The system of claim 1 wherein the catheter and the guiderail are separate and distinct members.

4. The system of claim 1 wherein the guiderail further includes a stiffer segment, the stiffer segment being at least partially constructed of a material that is stiffer than that of the guiderail housing, the stiffer segment positioned substantially parallel to at least one of the first guidewire lumen and the second guidewire lumen.

5. The system of claim 4 wherein the stiffer segment is positioned between the first guidewire lumen and the second guidewire lumen of the guiderail housing.

6. The system of claim 4 wherein the first guidewire lumen and the second guidewire lumen of the guiderail housing are positioned on the same side of the stiffer segment.

7. The system of claim 1 wherein the catheter includes a balloon disposed about at least a portion of a distal region of the catheter, wherein the balloon is disposed coaxially with the first guidewire lumen of the catheter.

8. The system of claim 7 wherein the second guidewire lumen of the catheter is provided exterior to the balloon.

9. The system of claim 8 further comprising a stent disposed about at least a portion of the balloon.

* * * * *